United States Patent
Adolph et al.

(10) Patent No.: US 7,145,003 B1
(45) Date of Patent: Dec. 5, 2006

(54) PROCESS FOR SYNTHESIZING 1,5 DINOSYL-3,3,7,7-TETRAKIS(DIFLUOR-AMINO)OCTAHYDRO-1,5-DIAZOCINE (DNTDFD)

(75) Inventors: Horst G. Adolph, Warrenton, VA (US); Alfred G. Stern, Upper Marlboro, MD (US)

(73) Assignee: The United States of America as represented by the Secrectary of the Navy, Washington, DC (US)

( * ) Notice: Subject to any disclaimer, the term of this patent is extended or adjusted under 35 U.S.C. 154(b) by 302 days.

(21) Appl. No.: 10/719,856

(22) Filed: Nov. 24, 2003

(51) Int. Cl.
*C07D 245/02* (2006.01)

(52) U.S. Cl. ..................................... 540/470

(58) Field of Classification Search ................ 540/470
See application file for complete search history.

(56) References Cited

U.S. PATENT DOCUMENTS

| | | | |
|---|---|---|---|
| 6,310,204 B1 | 10/2001 | Chapman et al. | 544/242 |
| 6,395,899 B1 | 5/2002 | Chapman et al. | 544/322 |
| 6,417,355 B1 | 7/2002 | Chapman et al. | 540/466 |
| 2002/0007063 A1 | 1/2002 | Chapman et al. | 544/316 |
| 2002/0161248 A1 | 10/2002 | Chapman et al. | 549/451 |

*Primary Examiner*—James O. Wilson
*Assistant Examiner*—Ebenezer Sackey
(74) *Attorney, Agent, or Firm*—Fredric Zimmerman

(57) ABSTRACT

A process for synthesizing 1,5-Dinosyl-3,3,7,7-tetrakis(difluoramino) octahydro-1,5-diazocine (DNTDFD) by reacting tetrahydro-1,5-bis(4-nitrobenzenesulfonyl)-1,5-diazocine-3,7-(2H, 6H) dione with $HNF_2$/oleum initially approximately between −5 and 0 degrees C., and allowing the temperature to rise to between 10 degrees C. and ambient temperature during said reaction to initiate difluoramination producing product DNTDFD. A 2:1 mixture of FREON® 11 refrigerant and pentane or cyclopentane, or pentane alone is used as a diluent and absorbent for the reagent difluoramine. The present invention reduces the time required to produce DNTDFD from about two weeks to one to three days and reduces the need to use relatively large quantities of FREON® 11, a compound which is damaging to the environment.

15 Claims, 1 Drawing Sheet

PROCESS FOR SYNTHESIZING 1,5 DINOSYL-3,3,7,7-TETRAKIS(DIFLUOR-AMINO)OCTAHYDRO-1,5-DIAZOCINE (DNTDFD)

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention relates to the production of solid fuel propellant oxidizers and, in particular, to an improved process for synthesizing 1,5-Dinosyl-3,3,7,7-tetrakis (difluoramino)-octahydro-1,5-diazocine (DNTDFD), which is a critical intermediate compound used in the production of 3,3,7,7-tetrakis (difluoramino) octahydro-1,5-dinitro-1,5-diazocine (HNFX), an efficient explosive and solid fuel propellant oxidizer.

2. Description of the Background

The compound HNFX is a valuable component in rocket propellant formulations because of its high explosive and oxidizing properties. HNFX is synthesized from commercially available materials using a multiple step process. The initial phase of some known processes leads to the intermediate compound DNTDFD, a critical intermediate for certain effective methods of producing HNFX. DNTDFD is processed into HNFX by one of a variety of methods, some of which are detailed in "Nitrolysis of a Highly Deactivated Amide by Protonitronium. See, *Synthesis and Structure of HNFX*, Robert D. Chapman, Journal of Organic Chemistry (1999, 64, 960–965).

The known methods for producing DNTDFD are described in *Difluoramination of Heterocyclic Ketones: Control of Microbasicity*, Robert D. Chapman, Journal of Organic Chemistry (1998, 63, 1566). The compound HNFX is similar to another explosive and propellant oxidizer, TNFX. The process of preparing TNFX is detailed in U.S. Patent Application No. 2000/0161248, to Chapman and in U.S. Pat. No. 6,417,355, also to Chapman. The precursor to TNFX is a compound very similar to DNTDFD. Both compounds are synthesized by a lengthy process requiring fluctuating temperature conditions. In preparing the precursor to TNFX, the reaction proceeds slowly and must be encouraged by cycling the temperature between −15 degrees C. and 0 degrees C. throughout the process, which reaches completion in two weeks time.

The process of preparing DNTDFD, as described in *Difluoramination of Hetrerocyclic Ketones: Control of Microbasicity*, Robert D. Chapman, Journal of Organic Chemistry (1998, 63, 1566 at 1570), requires a solution of fuming sulfuric acid, to which $CH_2Cl_2$ is added and cooled to −15 degrees C. Gaseous $HNF_2$ is absorbed into the layer of $CH_2Cl_2$. The temperature is raised, briefly, so that the HNF2, may be absorbed and the mixture is recooled. Tetrahydro-1,5-bis(4-nitrobenzenesulfonyl)-1,5-diazocine-3,7-(2H, 6H) dione is added to the mixture, which is stirred for 15 days. The solution is basified and precipitated. The product, DNTDFD, is obtained. During the course of the reaction, temperature is allowed to rise gradually from −15 degrees C. to −8 degrees C. An alternate method is described, which involves the absorption of $HNF_2$ gas into a layer of FREON® 11 trichlorofluoromethane and the addition of tetrahydro-1,5-bis(4-nitrobenzenesulfonyl)-1,5-diazocine-3,7-(2H, 6H) dione. This method involves cycling the temperature between −15 degrees C. and 0 degrees C. and requires 11 days.

Typically, FREON® 11 solvent is used as a diluent and absorbent for the difluoramine reagent. The process produces a yield of 52% of (crude) DNTDFD.

The DNTDFD is then processed into HNFX by one of the methods referenced above. There is a need for a more efficient process, which can more quickly and economically produce the intermediate compound, DNTDFD.

SUMMARY OF THE INVENTION

Accordingly, it is an object of the present invention to provide a process for more quickly synthesizing DNTDFD, in an efficient manner.

It is a further object to provide a process requiring a reduced amount of FREON® 11, a compound which is damaging to the environment.

In accordance with the stated objects, a process is provided for synthesizing the critical intermediate compound, DNTDFD. The precursor of DNTDFD, tetrahydro-1,5-bis (4-nitrobenzenesulfonyl)-1,5-diazocine-3,7-(2H, 6H) dione, is formed by oxidation of dinosyldiazocinediol. Known means are used to produce the oxidation reaction and yield tetrahydro-1,5 bis (4-nitrobenzenesulfonyl)-1,5-diazocine-3,7-(2H, 6H) dione.

The novelty in the present invention comprises initiating a reaction of tetrahydro-1,5-bis-(4-nitrobenzenesulfonyl)-1,5-diazocine-3,7-(2H, 6H) dione with HNF2/oleum, to achieve difluoramination. The reaction is initiated at a temperature between approximately −5 and 0 degrees C. The temperature is allowed to rise to between 10 degrees C. and ambient temperature during the course of the reaction. The reaction completes in one to three days and yields up to 61% (crude) DNTDFD. A 2:1 mixture of FREON® 11 refrigerant and pentane or cyclopentane, or pentane alone, is used as a diluent and absorbent for the reagent difluoramine. After the reaction begins, it is not necessary to monitor the temperature or to continue to cool the constituent compounds; although the yield improves if the compounds are cooled.

The present invention reduces the time required to produce DNTDFD from about two weeks to one to three days and reduces the need to use relatively large quantities of FREON® 11, a compound which is damaging to the environment.

DETAILED DESCRIPTION OF THE PREFERRED EMBODIMENTS

Figure 1:
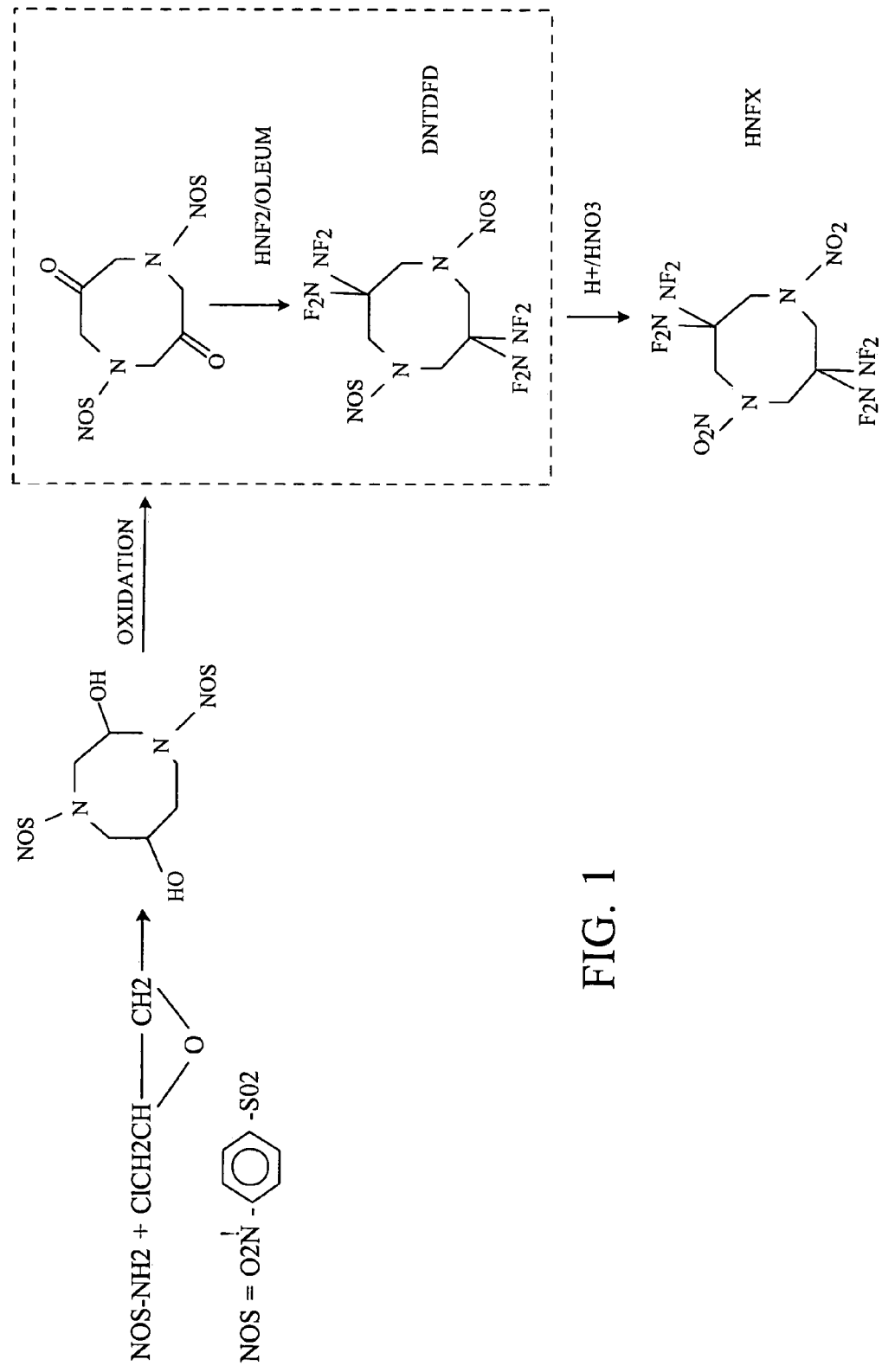
FIG. 1 is a schematic drawing illustrating the chemical process for more quickly synthesizing DNTDFD with reduced FREON® 11, according to the present invention.

The present invention is an improved process for synthesizing 1,5-Dinosyl-3,3,7,7-tetrakis (difluoramino) octahydro-1,5-diazocine (DNTDFD), which is a critical intermediate compound used in the production of 3,3,7,7-tetrakis (difluoramino)-octahydro-1,5-dinitro-1,5-diazocine (HNFX), an efficient explosive and solid fuel propellant oxidizer.

FIG. 1 is a schematic drawing illustrating the chemical process according to the present invention.

The precursor of DNTDFD, tetrahydro-1,5-bis(4-nitrobenzenesulfonyl)-1,5-diazocine-3, 7-(2H, 6H) dione, is formed by oxidation of dinosyldiazocinediol in a conventional manner. A suitable (and typical) process for this is described in the article entitled "*Difluoramination of Heterocyclic Ketones: Control of Microbasicity*", Robert D. Chapman, (cited above). The compound, DNTDFD is then prepared directly from tetrahydro-1,5-bis-(nitrobenzenesulfonyl)-1,5-diazocine-3,7-(2H 6H) dione, by difluoramination. The process of the present invention simplifies this step.

As shown in FIG. 1 (dotted lines) a reaction of tetrahydro-1,5-bis(4-nitrobenzenesulfonyl) 1,5-diazocine-3,7-(2H, 6H) dione with HNF2/oleum is initiated to achieve difluoramination. The reaction is initiated at between approximately −5 and 0 degrees C. The temperature is allowed to rise to approximately between 10 degrees C. and ambient temperature during the course of the reaction. The reaction completes in one to three, days and yields up to 61% of (crude) DNTDFD. A 2:1 mixture of FREON® 11 with pentane or cyclopentane, or pentane alone, is used as a diluent and absorbent for the reagent difluoramine. After the reaction begins, it is not necessary to monitor the temperature or to continue to cool the constituent compounds; although the yield improves if the compounds are cooled.

The DNTDFD is then processed into HNFX by one of the known methods referenced above.

The present method reduces the time required to produce DNTDFD from approximately two weeks to one to three days and reduces the need to use relatively large quantities of FREON® 11, a compound which is damaging to the environment.

The savings in time and the reduced need for FREON® 11 represent a significant advantage in the production of the valuable compound HNFX.

The following examples illustrate the processes described herein:

EXAMPLE 1

Difluoramination of 1,5-Dinosyltetrahydro-1,5-diazocine-3,7-dione at Room Temperature. CAUTION: Difluoramine and the difluoramino compounds described here are explosives and must be handled using appropriate safety measures. Difluoramine was generated from aqueous difluorurea solution (from 6.6 g urea and 125 ml of water) by the standard procedure (Chapman et al, J. Org. Chem. (1998, 63, 1566)). It is advisable to generate most of the difluoramine slowly at a temperature between 50 and 70 degrees C. to avoid sudden increases of difluoramine concentration. After drying by passing through a cold trap cooled with ice, then through a column of Drierite, the difluoramine/nitrogen gas stream was passed into the reaction flask above the liquid level.

The reaction vessel was a 50 ml, three-neck flask. It was fitted with a Dewar-type dry-ice condenser (to be filled with dry-ice/acetone) vented via a bubbler, an L-tube for solids addition, and a magnetic stirring bar.

The substrate, 0.906 g, was added to the L-tube. The system was purged with dry nitrogen for about an hour. The condenser was charged with coolant. 30% Oleum, 7 mL, was added to the reaction flask followed by 10 mL of pentane (1) and 5 mL of FREON® 11. Stirring was initiated.

Difluoramine was generated as described above. About 0.5 hours after difluoramine generation was complete, the nitrogen flow was redirected to isolate the reaction vessel from the generation unit. Cooling of the reaction flask was started with an ice-water bath. Difluoramine was allowed to interact with the oleum for about 1 hour. With continued cooling the substrate was added slowly via the L-tube. 0.5 mL 100% sulfuric acid was added through the L-tube to help wash remaining substrate into the reaction flask.

After about an hour the nitrogen flow was redirected again to the exit of the dry-ice condenser, thus eliminating nitrogen flow through the reaction vessel. The dry-ice in the condenser was allowed to evaporate and was replaced by the immersion probe of a chiller capable of cooling the acetone in the condenser to −40 degrees C. The ice-water bath was allowed to warm to near room temperature over an hour and was then removed. The system was allowed to react overnight.

After a reaction time of 19 hours (from completion of substrate addition) the bottom layer (oleum phase) was added dropwise to crushed ice, using agitation to prevent local overheating. The ice was allowed to melt and the suspension was filtered. The product was dried in air, and thus was obtained 0.595 g (48%) of crude product.

The product had no carbonyl band in the IR and was easily and completely soluble in acetone. It showed a 19F signal at 28.7 ppm (d6-acetone), and a 1H signal at 4.36 ppm (CH2, d6-acetone).

(1) Pentane was purified by stirring with 30% oleum (20:1), followed by stirring of the pentane phase with MgSO4 and filtering. It was stored over molecular sieves.

EXAMPLE 2

The same procedure was used as in EXAMPLE 1. However, dry-ice/acetone was used for cooling the condenser during the day, and was allowed to evaporate over night. No additional cooling was used. The yield and purity of product was the same as in example 1.

EXAMPLE 3

The same procedure was used as in EXAMPLE 1, except that 11.6 mL of 30% oleum was used. The yield and purity of product was the same as in EXAMPLE 1.

EXAMPLES 4 AND 5

Difluoramination of 1,5-Dinosyl-perhydrodiazocine-3,7-dione at 10–15 degrees C. CAUTION: See example 1.

Difluoramine was generated from aqueous difluorurea solution (from 6.6 g urea and 100 ml of water) by the standard procedure as described in example 1. The difluoramine/nitrogen gas stream was passed through a cold trap cooled with ice, through a column of Drierite, and then into the reaction flask above the liquid level.

The reaction vessel was a 100 mL jacketed four-neck flask (ACE Glass). It was fitted with a Dewar-type dry-ice condenser (to be filled with dry-ice/acetone) vented via a bubbler, an L-tube for solids addition, and a magnetic stirring bar. The jacket was connected to a circulating bath with 1:1 ethyleneglycol/water as the cooling fluid.

The generating unit, reaction vessel, and bubbler were connected via appropriately placed T-stopcocks to allow redirecting the nitrogen flow directly into the reaction flask or directly into the bubbler as needed (see below). A flow of dry nitrogen was maintained throughout the experiment.

The substrate was added to the L-tube. The entire system was purged with dry nitrogen for about an hour. The condenser was charged with coolant. The reaction vessel was cooled to 10 degrees C. Stirring was initiated. Pentane (1) and FREON® 11 were added to the reaction vessel, followed by 30% oleum. Reagent amounts are shown in Table I.

Cold (<5 degree C.) difluorourea solution was added to the generating flask followed by dropwise addition with stirring of concentrated sulfuric acid (20 mL). Difluoramine generation was initiated as described above. After completion of acid addition to the difluorurea solution, the reaction vessel was cooled to 5 degrees C.; when the generating bath temperature had reached 50 degrees C., the reaction vessel was cooled to 0 degrees C. and difluoramine generation was completed. Difluoramine was allowed to interact with the oleum for 1 hour after completion of the generation. About 0.5 hours after completion of difluoramine generation, the nitrogen flow was redirected to isolate the reaction vessel from the generation unit and the reaction vessel was cooled to −5 degrees C. After another half hour, the nitrogen flow was redirected again to the exit of the dry-ice condenser, thus eliminating nitrogen flow through the reaction vessel.

The substrate (Table 1) was added slowly via the L-tube (15–30 minutes). The L-tube was removed and replaced by a stopper. The L-tube was rinsed with water and residual diketone was recovered, dried, and weighed. The reaction was allowed to proceed at −5 degrees C. for the time shown in Table 1, and the temperature was then gradually raised as indicated in Table 1.

During the warm-up period, the dry-ice in the condenser was allowed to evaporate and was replaced by the immersion probe of a chiller capable of cooling the acetone in the condenser to −40 degrees C. The system was allowed to react at 10 or 15 degrees C. for the time shown in Table 1.

At the end of the reaction period the reaction flask was cooled to 0 degrees C. and the contents of the flask were transferred to a separatory funnel. The bottom layer was added dropwise to crushed ice with agitation. The solids were filtered off, washed with water, triturated with an aqueous solution of sodium bicarbonate (see Table 1), filtered again and washed with water. After drying in air at 50 degrees C., the crude product was weighed and was characterized by 1 H and 19F NMR and by HPLC.

TABLE 1

Reaction Conditions and Reagent Amounts for Two Difluoramination Runs with Different Difluoramine/Substrate Ratios (Examples 4 and 5).

| | Example 4 | Example 5 |
|---|---|---|
| Urea (g; mmol) used to make difluoramine | 6.6; 100 | 6.6; 100 |
| Water (mL) | 100 | 100 |
| Conc. H2S04 for difluoramine generation (mL) | 20 | 20 |
| Pentane (mL) | 5.5 | 9.5 |
| FREON ® 11 (mL) | 2.75 | 5 |
| 30% Oleum (mL) | 5.25 | 9.3 |
| Dione substrate (g; mmol) | 0.68; 1.33 | 1.205; 2.35 |
| NaHC03 (g) | 1 | 1 |
| Reaction conditions after completion of substrate addition (h/° C.) | 0/−5; 1.5/0; 1/5; 63/10 | 2/−5; 2/0; 16/5; 1/10; 46/15 |
| Crude yield (g; % of theory) | 0.55; 60.2 | 0.84; 52.0 |
| HPLC analysis (area % of DNTDFD peak) | 60.3 | 57.1 |
| Apparent yield (crude yield × area % DNTDFD) | 36.3 | 29.7 |

(1) Pentane was purified by stirring with 30% oleum (20:1), followed by stirring of the pentane phase with MgSO4 and filtering. It was stored over molecular sieves.

EXAMPLE 6

The same procedure was used as in Example 4, except that 8.25 mL of pentane and no FREON® 11 was used. The yield and purity of the product were substantially the same as in Example 4.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the following claims.

We claim:

1. A process for synthesizing the compound 1,5-Dinosyl-3,3,7,7-tetrakis(difluoramino) octahydro-1,5-diazocine (DNTDFD), comprising:
   reacting tetrahydro-1,5-bis(4-nitrobenzenesulfonyl)-1,5-diazocine-3,7-(2H, 6H) dione with HNF2/oleum, in the presence of a diluent and absorbent for the reagent difluoramine, initially approximately between −5 and 0 degrees C.; and
   allowing a temperature to rise to between 10 degrees C. and ambient temperature during said reaction, to yield crude DNTDFD.

2. The process of claim 1, wherein said reacting tetrahydro-1,5-bis(4-nitrobenzenesulfonyl)-1,5-diazocine-3,7-(2H, 6H) dione with HNF2/oleum further comprises stirring.

3. The process of claim 1, wherein said diluent and said absorbent is a 2:1 mixture selected from one of trichlorofluoromethane with pentane and trichlorofluoromethane with cyclopentane.

4. The process of claim 1, wherein said diluent and said absorbent is a 2:1 mixture selected from one of pentane and cyclopentane with trichlorofluoromethane.

5. The process of claim 1 wherein said diluent and said absorbent is one of pentane and cyclopentane.

6. The process of claim 1, further comprising cooling the -1,5-bis(4-nitrobenzenesulfonyl)-1,5-diazocine-3,7-(2H, 6H) dione, the HNF2/oleum and the diluent and the absorbent, to a temperature between approximately −5 and 0 degrees C. before allowing the temperature to rise.

7. The process of claim 1, wherein said reacting tetrahydro-1,5-bis(4-nitrobenzenesulfonyl)-1,5-diazocine-3,7-(2H, 6H) dione with HNF2/oleum, in the presence of said diluent and said absorbent for the reagent difluoramine, comprises combining said HNF2/oleum and said diluent and said absorbent for a time of approximately one hour before adding the tetrahydro-1,5 bis(4-nitrobenzenesulfonyl)-1,5-diazocine-3,7-(2H, 6H) dione.

8. The process of claim 1, further comprising cooling said crude DNTDFD solution, adding it to crushed ice, filtering, adding a triturating solution, filtering and drying.

9. The process of claim 8, wherein the triturating solution is aqueous sodium hydrogen carbonate.

10. A process for synthesizing the compound 1,5-Dinosyl-3,3,7,7-tetrakis(difluoramino) octahydro-1,5-diazocine (DNTDFD), comprising:
   reacting tetrahydro-1,5-bis(4-nitrobenzenesulfonyl)-1,5-diazocine-3,7-(2H, 6H) dione with HNF2/oleum initially approximately between −5 and 0 degrees C.; and allowing a temperature to rise to between 10 degrees C. and ambient temperature during said reaction to yield crude DNTDFD.

11. The process of claim 10, wherein said reacting tetrahydro-1,5-bis(4-nitrobenzenesulfonyl)-1,5-diazocine-3,7-(2H, 6H) dione with HNF2/oleum further comprises stirring.

12. The process of claim 11, further comprising adding a diluent and an absorbent comprising at least one of pentane, FREON® 11, and pentane and FREON® 11.

13. The process of claim 11, further comprising adding a diluent and an absorbent comprising at least one of pentane, trichlorofluoromethane, and pentane and trichlorofluoromethane; and cooling the tetrahydro-1,5-bis(4-nitrobenzenesulfonyl)-1,5-diazocine-3,7-(2H, 6H) dione with HNF2/oleum to a temperature between approximately −5 and 0 degrees C., before allowing the temperature to rise.

14. A process for synthesizing the compound 1,5-Dinosyl-3,3,7,7-tetrakis(difluoramino) octahydro-1,5-diazocine (DNTDFD), comprising:

reacting tetrahydrol, 5-Dinosyl-perhydrodiazocine-3,7-dione with HNF2/oleum, in the presence of a diluent and absorbent for the reagent difluoramine, initially approximately between −5 and 0 degrees C.; and allowing a temperature to rise to between 10 degrees C. and 15 degrees C. during said reaction, to yield crude DNTDFD.

15. The process of claim 14, further comprising adding said diluent and said absorbent comprising at least one of pentane, trichlorofluoromethane, and pentane and trichlorofluoromethane.

* * * * *